United States Patent
Pinto et al.

(10) Patent No.: US 8,834,521 B2
(45) Date of Patent: Sep. 16, 2014

(54) SUTURING CONSTRUCT WITH SPLICED TAILS

(75) Inventors: Mark C. Pinto, Ann Arbor, MI (US); Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 620 days.

(21) Appl. No.: 12/646,786

(22) Filed: Dec. 23, 2009

(65) Prior Publication Data
US 2010/0160962 A1 Jun. 24, 2010

Related U.S. Application Data

(60) Provisional application No. 61/140,552, filed on Dec. 23, 2008.

(51) Int. Cl.
*A61B 17/04* (2006.01)
*A61B 17/06* (2006.01)
*A61F 2/08* (2006.01)

(52) U.S. Cl.
CPC ......... *A61B 17/06166* (2013.01); *A61F 2/0805* (2013.01); *A61F 2/0811* (2013.01); *A61B 2017/0414* (2013.01); *A61B 17/0469* (2013.01); *A61F 2002/0858* (2013.01); *A61F 2002/0888* (2013.01); *A61B 17/0401* (2013.01)
USPC .......................................... 606/228; 606/232

(58) Field of Classification Search
CPC .................... A61B 17/06166; A61B 17/0401; A61L 17/04; A61F 2/0811
USPC .................................. 606/228, 232
See application file for complete search history.

(56) References Cited

U.S. PATENT DOCUMENTS

| | | | |
|---|---|---|---|
| 4,662,886 A | 5/1987 | Moorse et al. | |
| 5,830,234 A | 11/1998 | Wojciechowicz et al. | |
| 5,891,168 A * | 4/1999 | Thal | 606/232 |
| 6,506,197 B1 * | 1/2003 | Rollero et al. | 606/148 |
| 6,716,234 B2 | 4/2004 | Grafton et al. | |
| 7,029,490 B2 | 4/2006 | Grafton et al. | |
| 2003/0130694 A1 * | 7/2003 | Bojarski et al. | 606/228 |
| 2004/0093031 A1 | 5/2004 | Burkhart et al. | |
| 2005/0192631 A1 | 9/2005 | Grafton | |
| 2007/0191849 A1 | 8/2007 | ElAttrache et al. | |

(Continued)

FOREIGN PATENT DOCUMENTS

EP 0 494 636 A1 7/1992

OTHER PUBLICATIONS

Knotless Rotator Cuff Repair, Speedbridge and Speedfix Knotless Rotator Cuff Repair Using the Swivelock C and FiberTape, Surgical Technique, Arthrex, Inc., 2010.

*Primary Examiner* — Gregory Anderson
*Assistant Examiner* — Christina Lauer
(74) *Attorney, Agent, or Firm* — Dickstein Shapiro LLP

(57) ABSTRACT

A surgical construct having a flexible strand with a middle region and at least two opposing tail regions that are spliced to form a single tail. The middle region has a first diameter and the opposing tail regions have a second diameter, which is smaller than the first diameter. The tail regions may have similar or different diameters. Because of the thin spliced tail regions, the suturing construct of the present invention can be easily inserted into suture/tape passing and retrieving instruments and passed through soft tissue (such as a rotator cuff). Once the suturing construct has been passed through tissue, the splice may be cut to allow the suture/tape to have again individual tails.

4 Claims, 7 Drawing Sheets

(56) References Cited

U.S. PATENT DOCUMENTS

| | | |
|---|---|---|
| 2007/0213770 A1 | 9/2007 | Dreyfuss |
| 2007/0219558 A1* | 9/2007 | Deutsch .......................... 606/72 |
| 2008/0004659 A1 | 1/2008 | Burkhart et al. |
| 2008/0281357 A1 | 11/2008 | Sung et al. |

* cited by examiner

SUTURING CONSTRUCT WITH SPLICED TAILS

CROSS-REFERENCE TO RELATED APPLICATIONS

This application claims the benefit of U.S. Provisional Application No. 61/140,552, filed Dec. 23, 2008, the entire disclosure of which is incorporated by reference herein.

FIELD OF THE INVENTION

The present invention relates to surgical sutures and, more particularly, to a suture with spliced tails.

BACKGROUND OF THE INVENTION

The SutureBridge™ tendon repair technique, developed by Arthrex, Inc., and disclosed in U.S. Patent Publication No. 2007/0191849, the disclosure of which is herein incorporated by reference, consists of a tied medial row constructed with two threaded suture anchors, combined with knotless lateral fixation using two Arthrex PushLock® anchors. The construct, shown in FIG. 1A, enhances footprint compression and promotes tendon healing-to-bone with minimal knot tying.

The SpeedBridge™ technique, also developed by Arthrex, Inc., uses a threaded swivel anchor (such as disclosed in U.S. Patent Publication No. 2008/0004659, the disclosure of which is herein incorporated by reference) combined with FiberTape® (disclosed in U.S. Patent Publication No. 2005/0192631), the disclosure of which is herein incorporated by reference) to create a quick and secure SutureBridge construct with no knots and only two suture passing steps.

In the SpeedBridge™ technique, a swivel anchor, preferably an Arthrex 4.75 mm SwiveLock® C, loaded with one strand of FiberTape®, is inserted into a medial bone socket. A suture shuttle such as FiberLink™ is used to shuttle both FiberTape® tails through the rotator cuff simultaneously. A FiberLink™ tail is passed through the rotator cuff using a suture passing instrument such as the Scorpion™. The tails of the FiberTape® are loaded through the FiberLink™ loop and shuttled through the rotator cuff. These steps are repeated for the second medial row anchor.

FIG. 1B depicts the SwiveLock® C loaded with one strand of FiberTape® being inserted into the bone socket.

Next, as shown in FIG. 1C, one FiberTape® tail from each medial anchor is retrieved and loaded through the SwiveLock® C eyelet. The loaded eyelet is inserted into a prepared lateral bone socket until the anchor body contacts bone, and the tension is adjusted if necessary.

The SwiveLock® C driver is rotated in a clockwise direction to complete the insertion. Using a cutter, the FiberTape® tails are cut, one and a time, to complete the technique. A completed suture in accordance with the SpeedBridge™ technique is shown in FIG. 1D.

In the above-described SpeedBridge™ technique, it can be difficult to shuttle (pass) the two FiberTape® tails through the rotator cuff simultaneously. Accordingly, it would be desirable to provide a length of FiberTape® with a splice leading to a single tail that can be easily loaded into the tissue passing instrument, and then cut to again have two FiberTape® tails for completing the SpeedBridge™ construct.

SUMMARY OF THE INVENTION

The present invention fulfills the needs noted above by providing a surgical construct comprising a flexible strand with both opposing ends terminating in a same single tail. The invention provides a suture or tape construct having a middle region and at least two opposing tail regions that are spliced to form a single tail. The middle region preferably has a first diameter and the opposing tail regions have a second diameter which is smaller than the first diameter. The tail regions may have similar or different diameters from each other.

Because of the thin spliced tail region, the suture construct of the present invention can be more easily inserted into suture/tape passing and retrieving instruments and passed through tissue than regular suture/tape. After the suture or tape is passed through tissue, the splice can be cut to have again two tails of suture or tape.

The invention also provides a system for surgical repairs comprising: a fixation device comprising an anchor body or a screw and an eyelet; and a suture construct comprising a flexible strand with both opposing ends terminating in a same single tail, wherein the flexible strand is configured in the form of a flexible loop with a splice leading to the tail, and wherein the flexible loop comprises a first region of a first diameter and two regions of a second diameter, the first diameter being greater than the second diameter, the suture construct being pre-loaded on the fixation device, the flexible loop being threaded through the eyelet of the fixation device.

These and other features and advantages of the present invention will become apparent from the following description of the invention that is provided in connection with the accompanying drawings and illustrated embodiments of the invention.

DETAILED DESCRIPTION OF THE INVENTION

The present invention provides a surgical construct having a middle region and at least two opposing tail regions that are spliced to form a single tail. The middle region has a first diameter and the opposing tail regions have a second diameter, which is smaller than the first diameter. The tail regions may have similar or different diameters. Because of the thin spliced tail regions, the suturing construct of the present invention can be easily inserted into suture/tape passing and retrieving instruments (such as the Arthrex Scorpion™) and passed through soft tissue (such as a rotator cuff). Once the suturing construct has been passed through tissue, the splice may be cut to allow the suture/tape to have again individual tails.

Figure 1A:
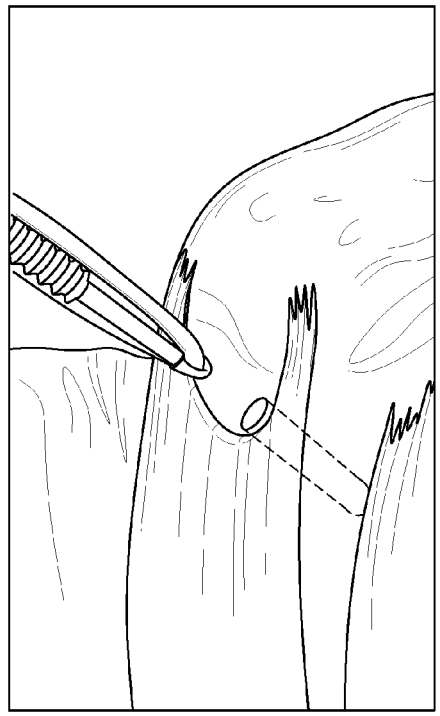
FIGS. 1A-1D illustrate tendon repair techniques.
Figure 1B:
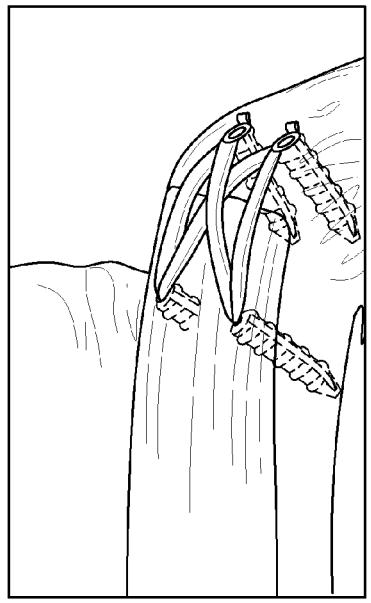
Figure 1C:
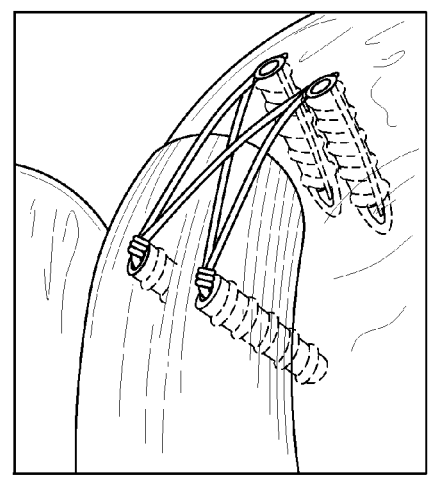
Figure 1D:
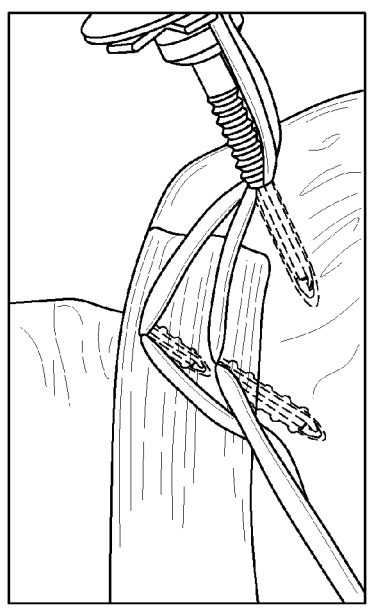
Figure 2:
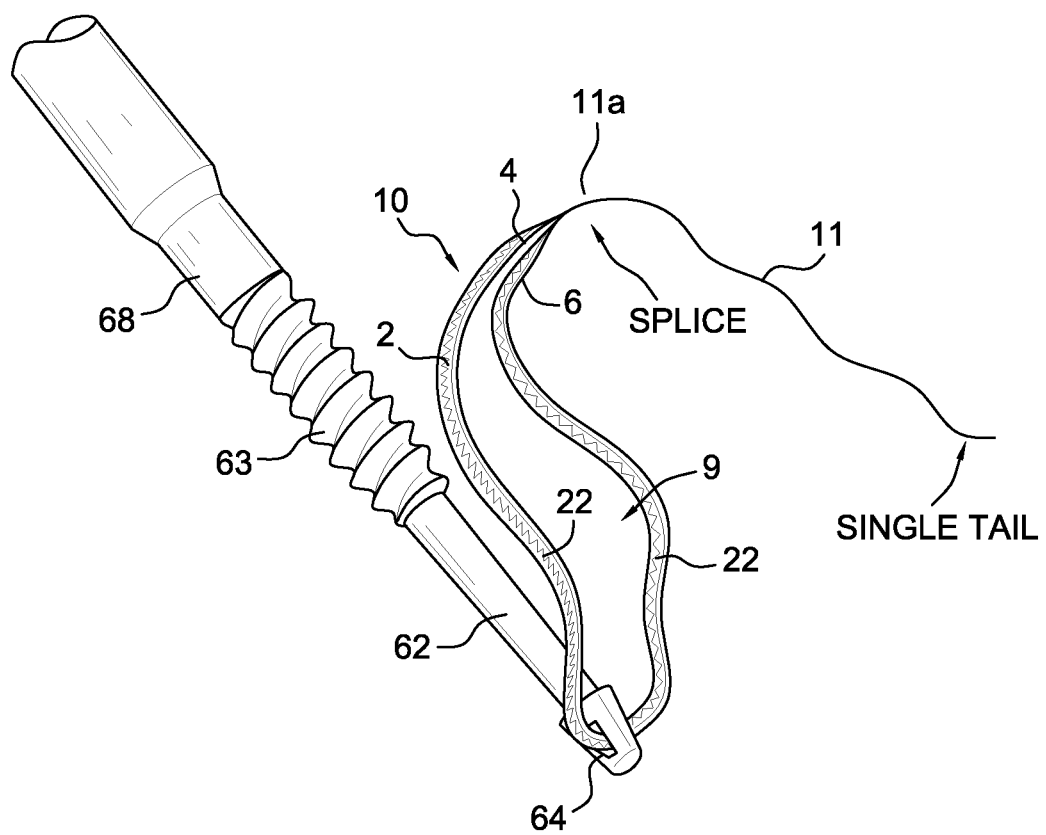
FIG. 2 illustrates a suturing construct with spliced tails according to an exemplary embodiment of the present invention.

Referring now to the drawings, where like elements are designated by like reference numerals, FIG. 2 illustrates an exemplary embodiment of a length of surgical construct 10 with spliced tails according to the present invention. Although the invention will be described below with reference to a suture tape construct with two tails, the invention also contemplates embodiments wherein the construct is a large diameter suture, or a combination of suture and tape, or wherein the construct includes multiple strands of suture or suture tape with any number of tails (at least two of the tails being spliced).

According to an exemplary embodiment only, the suturing construct 10 is formed of a flexible strand with a middle region 2 (suture section 2) which is adjacent two tail regions 4 and 6 and a splice (or single tail) 11. As shown in FIG. 2, the diameter of the tail region 4 may be similar to or different than the diameter of the tail region 6. In any event, each of the diameters of the tail regions 4, 6 is smaller than the diameter of the middle region 2.

In an exemplary embodiment, the middle region 2 (suture section 2) of the suturing construct 10 has a gradual taper in diameter (for example, from a #2 to #0 from section 2 to sections 4, 6 and single tail 11) made on a braiding machine. The single tail 11 of the construct 10 may be formed by splicing together the tail regions 4, 6 through splice 11a. The splice 11a may be done in a manner that provides a smooth transition. In another embodiment, the splice 11a and the single tail 11 may be formed by joining together at least a portion of each of tail regions 4, 6 to form flexible loop 9 and single tail 11. The joining of at least a portion of each of tail regions 4, 6 may be accomplished by braiding the tail regions, or by gluing them, or by other known method in the art. As a result of the smaller diameter of the tail regions 4, 6, and of the single tail 11, the suturing construct 10 of the present invention is more easily threaded through a suture passing instrument, and passed through tissue.

Middle section 2 may have cross-sections of various forms and geometries, including round, oval, rectangular, or flat, among others, or combination of such forms and geometries. In an exemplary embodiment only, section 2 may be provided as a suture tape or as a round suture, or as a combination of tape and round suture. The diameter of middle section 2 may be constant or may vary. Preferably, the diameter of section 2 is constant and is greater than the diameter of sections 4, 6 and of the spliced single tail 11.

FIG. 2 illustrates suturing construct 10 threaded through a knotless fixation device 62 such as an Arthrex PushLock® C anchor (as disclosed and described in U.S. Patent Application Publication No. 2004/0093031, the disclosure of which is incorporated by reference in its entirety) or an Arthrex SwivelLock® C anchor (as shown in FIG. 2, and as disclosed and described in U.S. Patent Application Publication No. 2007/0191849, the disclosure of which is incorporated by reference in its entirety). The fixation device 62 comprises an anchor body (or screw) 63 and an eyelet 64.

As shown in FIG. 2, construct 10 is pre-loaded (manufactured) on the fixation device 62 (i.e., the suture construct 10 is pre-loaded through eyelet 64 of the knotless fixation device 62 (SwiveLock® anchor 62)). As described in more detail below, the fixation device 62 with the pre-loaded suture construct 10 is first inserted into a bone socket or tunnel. Subsequent to the insertion into the bone socket, the tail 11 is passed through the tissue to be repaired. After passing the suture construct 10 through the tissue (with the advantage of a single tail 11), the splice is cut to open the loop of the construct and to form again two ends of the suture or suture tape. Each of the two ends may be employed further for tissue fixation, for example, the two ends may be individually threaded through additional eyelets of additional fixation devices and may be inserted in additional pilot holes (with additional fixation devices) to complete the suture repair system.

The spliced suture construct 10 of the present invention may be employed for various soft tissue to bone repairs that employ at least one knotless fixation device. According to an exemplary embodiment only, the surgical construct 10 of the present invention may be employed in a method for double row fixation of tendon to bone, as detailed in U.S. Patent Application Publication No. 2007/0191849. A method of exemplary tissue fixation with the surgical construct 10 of the present invention comprises inter alia the steps of: (i) providing surgical construct 10 pre-loaded (manufactured) on a fixation device (for example, a knotless fixation device); (ii) securing the fixation device with the pre-loaded construct 10 into a bone socket or tunnel; (iii) passing the suturing construct 10 through tissue to be repaired; (iv) removing the splice of the suturing construct 10 to release the two tail regions of the construct; and (v) employing at least one of the two released tail regions to fixate tissue.

Figure 3:
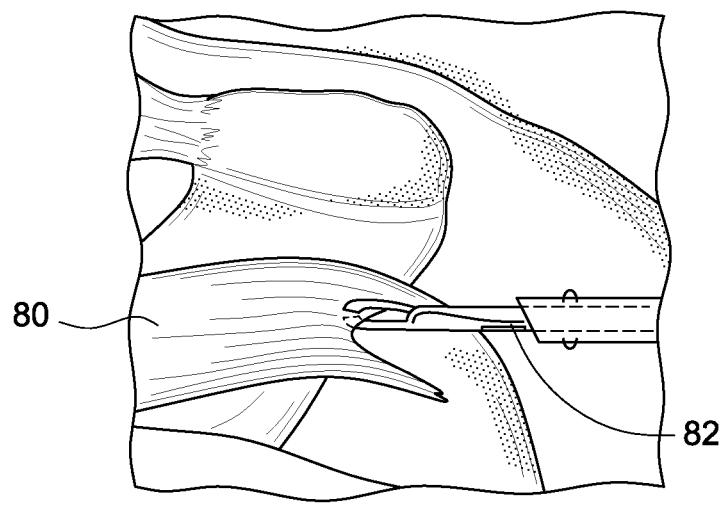
FIGS. 3-12 illustrate subsequent steps of a method of soft tissue repair (arthroscopic rotator cuff repair) with the suturing construct of FIG. 2, and according to an exemplary embodiment of the present invention.

Reference is now made to FIGS. 3-12 which illustrate subsequent steps of a method of soft tissue repair (arthroscopic rotator cuff repair) with the suturing construct 10 of FIG. 2, and according to an exemplary embodiment of the present invention. FIG. 3 illustrates a side view of a human shoulder of a patient undergoing a repair of rotator cuff 80 in accordance with an exemplary embodiment of the present invention. Although this particular embodiment will be illustrated below with reference to FIGS. 3-12 and with reference to only a particular knotless fixation device (such as Arthrex SwiveLock® C anchor), the invention is not limited to this particular embodiment and contemplates additional embodiments wherein any knotless fixation device may be employed, depending on the characteristics of the repair site and of the particular application.

The mobility of the tear is assessed using, for example, a tissue grasper 82 (FIG. 3) such as the Arthrex KingFisher™ Suture Retriever/Tissue Grasper, to determine whether a U or L-shaped component exists.

Figure 4:
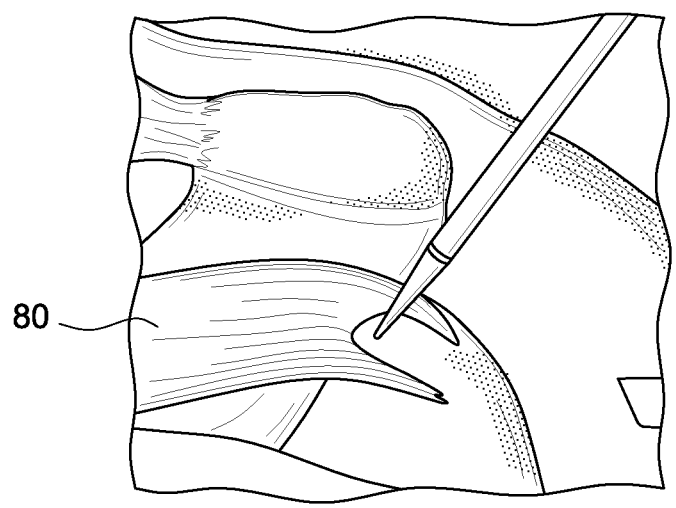
Figure 5:
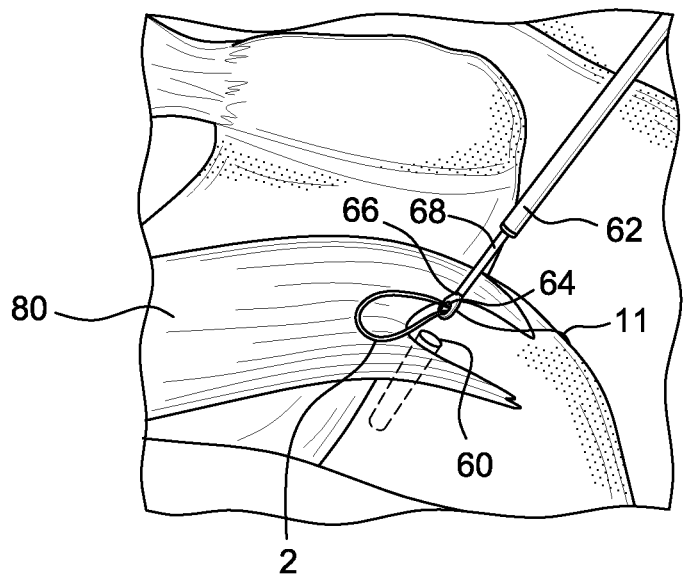
Figure 6:
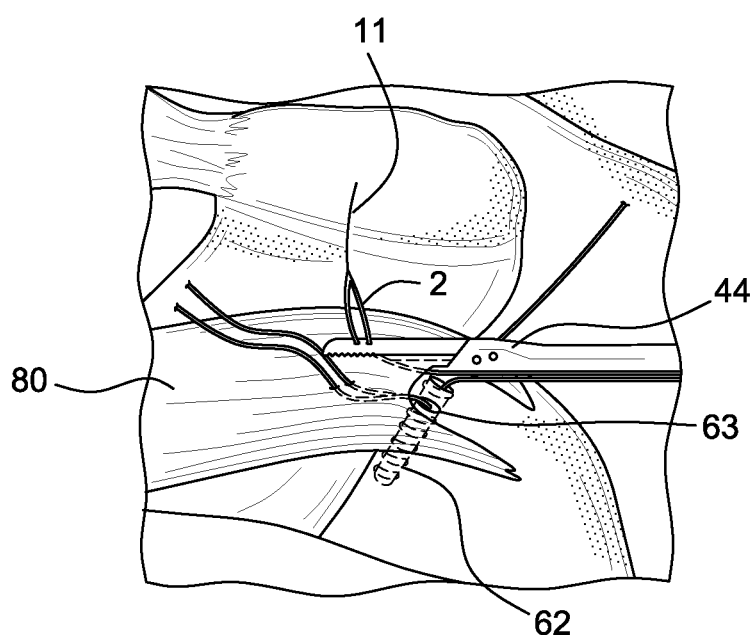
Figure 7:
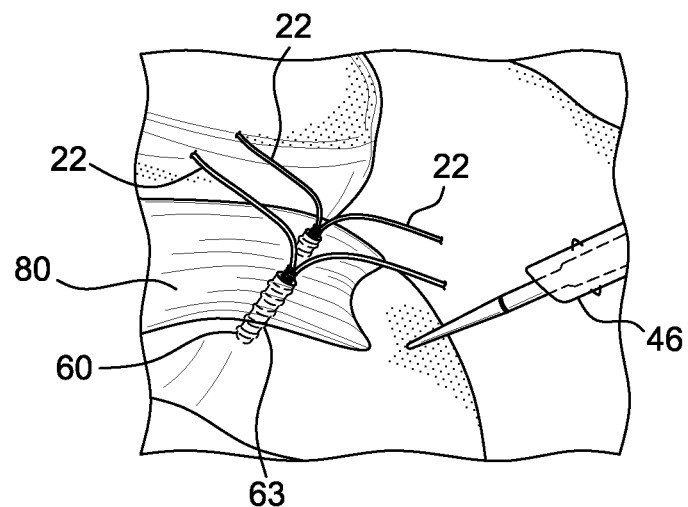
Figure 8:
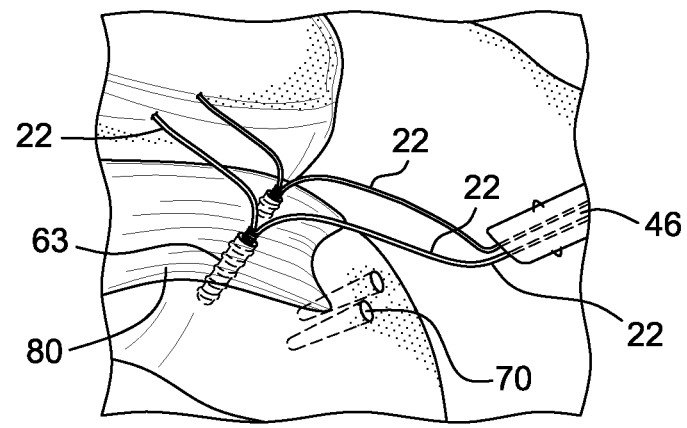
Figure 9:
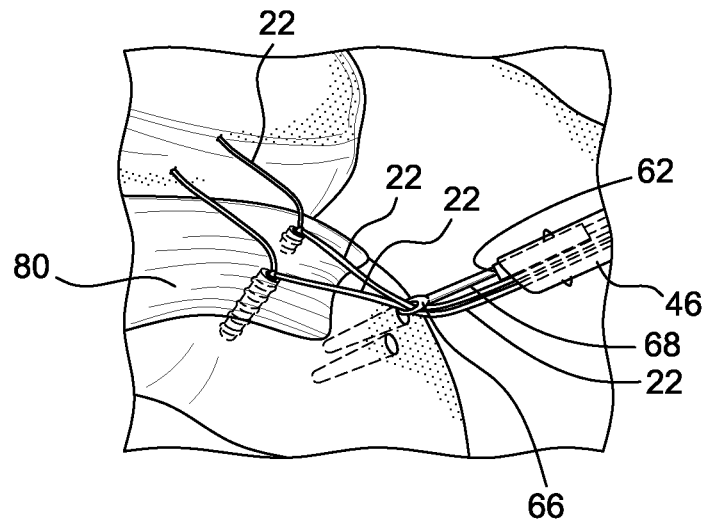
Figure 10:
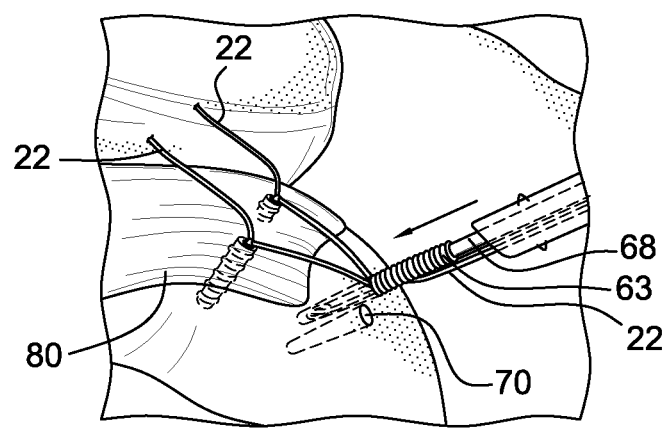
Figure 11:
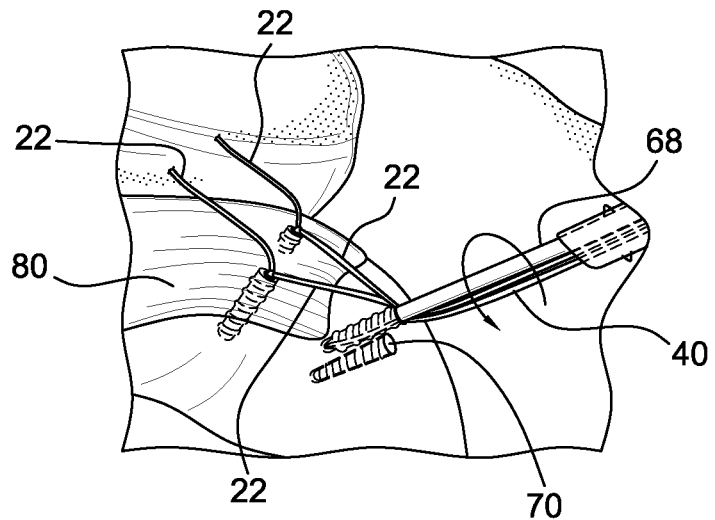

FIG. 4 illustrates the preparation of two pilot holes 60 for two suture anchors that will be inserted in the medial row. A punch may be employed adjacent to the articular margin of the humerus and at about 45 degree angle to form the two pilot holes. Subsequent to the formation of the pilot holes 60, and as shown in FIGS. 5-7, two fixation devices 62 with a pre-loaded suturing construct 10 are placed in the pre-formed holes 60 in the medial row. These fixation devices assure full contact of the detached tendon 80 along the medial footprint of the greater tuberosity.

As illustrated in FIG. 5, suturing construct 10 is pre-loaded (manufactured) on the fixation device 62, i.e., the suture construct 10 is pre-loaded through eyelet 64 of the knotless fixation device 62 (SwiveLock® anchor 62) on the distal end 66 of the driver 68.

Subsequently, and as shown in FIG. 5, the distal tip 66 of the knotless fixation device 62 (with the pre-loaded construct 10) is brought to the edge of the pilot hole 60. The driver 68 is then completely advanced into the pilot hole 60 until the anchor body or screw 63 contacts the bone. The driver is rotated in a clockwise direction, for example, to complete insertion. A mallet may be employed to impact the anchor body 63 into the pilot hole 60 until the anchor body is flush with the humerus. The driver 68 is then turned counterclockwise to disengage the eyelet 64 (within pilot hole 60) from the driver shaft. The steps described above are subsequently repeated for the second knotless fixation device 62 (for example, a second SwiveLock anchor) with another pre-loaded construct 10.

Subsequent to the securing of the knotless fixation devices 62 (with suturing construct 10 pre-loaded through eyelets 64 of the knotless fixation devices 62) within the bone sockets or tunnels, the tail 11 of the construct 10 is passed through the tissue to be repaired, i.e., through rotator cuff 80. For example, and as shown in FIG. 6, a suture shuttle (such as FiberLink™) and a suture passing instrument 44 (such as the Scorpion™) are used to shuttle tail 11 through the rotator cuff 80. The tail 11 of the construct 10 is loaded through the FiberLink™ loop and shuttled through the rotator cuff 80. Because of the thin spliced tail region 11, the suturing construct 10 of the present invention can be easily inserted into passing and retrieving instruments (such as the Arthrex FiberLink™ and/or Scorpion™) and passed easily through soft tissue (such as the rotator cuff 80).

Reference is now made to FIG. 7. Once the suturing construct 10 has been passed through tissue 80, the splice 11a is cut to allow the suture/tape to have again individual tails 22. FIG. 7 illustrates the two knotless fixation devices 62 with the two suturing constructs 10 having splices 11a removed (i.e., splice 11a is cut to open the loop 9 of the construct and to form again two tails 22 of each of the constructs).

Figure 12:
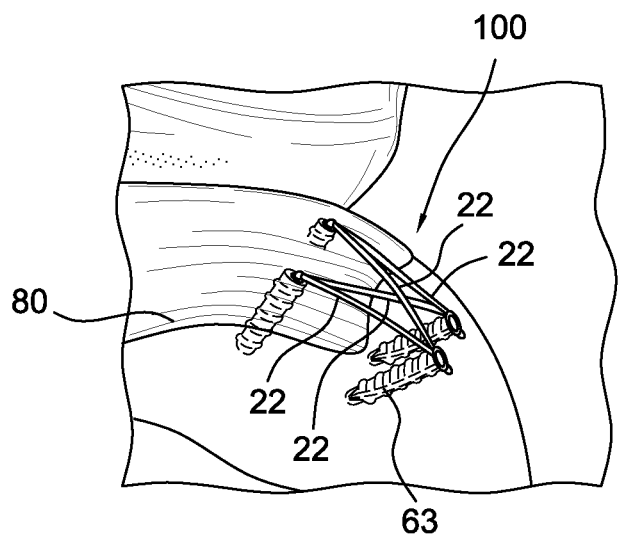

Each of the two ends 22 of the suture or suture tape may be employed further for tissue fixation, for example, each of the two ends may be threaded through additional eyelets of additional fixation devices and may be inserted in additional pilot holes (with additional fixation devices) to complete various suture repairs of the present invention. In an exemplary embodiment only, one tail 22 from each of the anchors 62 is retrieved and then loaded through another fixation device (for example, through another fixation device 62) and inserted within pilot holes 70 (FIGS. 9-11) of a lateral row of the suture repair 100 (FIG. 12). Tails 22 are inserted into prepared lateral bone sockets 70 until the anchor body contacts the bone. Tension is adjusted if necessary. The SwiveLock® driver is rotated in a clockwise direction to complete insertion. The tails 22 are cut, preferably one at a time, with an exemplary open-ended instrument (FiberWire® cutter) to complete formation of criss-cross suturing pattern 100 (FIG. 12) of the present invention.

The suturing construct 10 of the present invention described above may be formed of strands of a high strength suture material with surgically-useful qualities, including knot tie down characteristics and handling, such as Arthrex FiberWire® suture disclosed in U.S. Pat. No. 6,716,234, the disclosure of which is incorporated herein by reference. The suture construct may be formed of optional colored strands (preferably black) to assist surgeons in distinguishing between suture lengths with the trace and suture lengths without the trace. Preferably, each of tail regions 4, 6 may be provided in different colors to assist surgeons in retrieving one tail from each of the knotless fixation devices and then loading them through another fixation device, during the formation of the criss-cross suturing pattern 100 (FIG. 12).

Suturing construct 10 may be preferably coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture or tape, knot security, pliability, handleability or abrasion resistance, for example.

In additional embodiments, middle region 2 may be formed of polyester (for example, braided polyester) and the suture tail 11 may be also formed of polyester or a similar material. In an exemplary embodiment only, middle region 2 may be formed of braided polyester with a polyester core, and suture tail 11 may be braided polyester with a polyester core and spliced to the suture. The middle region and tail may be coated as detailed above. In addition, a coating may be provided to the yarns forming the suture construct 10 before braiding. Polyester yarns for the braided construct of the middle region 2 may be coated using a silicone elastomer (or a similar material as detailed above) prior to braiding. Similarly, the suture tails 4, 6 may be coated using the same or different coating material after braiding and before splicing. If desired, at least one of the tail regions 4, 6, 11 of suture construct 10 (preferably both tail regions 4, 6 and spliced tail 11) may be coated, impregnated, or otherwise stiffened with a material such as plastic, for example. Preferably, end tail 11 may have a very fine end that is coated, impregnated, or stiffened with a material such as plastic, for example.

Suture construct 10 may also contain a bioabsorbable material, such as PLLA or one of the other polylactides, for example, and/or may be formed of twisted fibers having strands of a contrasting color added to the braided threads, to make the suture more visible during surgical procedures. The colored strands, preferably, may be dyed filaments or strands.

The tail regions 4, 6 and the single tail 11 of the suture construct 10 may be also provided with tinted tracing strands, or otherwise contrast visually with the middle region of the suture construct, which remains a plain, solid color, or displays a different tracing pattern, for example. Accordingly, when the suture construct is loaded through the eyelet of a suture anchor or passed through tissue, for example, at least one of the tail regions 4, 6 of the suture construct, or the single tail 11, or the middle region 2, may be visually coded, making identification and handling of the suture legs simpler. Easy identification of suture in situ is advantageous in surgical procedures, particularly during arthroscopic surgeries, such as endoscopy and laparoscopy.

The suture construct 10 of the present invention has applicability to suture applications that may be employed in surgical procedures such as rotator cuff repair, Achilles tendon repair, patellar tendon repair, ACL/PCL reconstruction, hip and shoulder reconstruction procedures, and applications for suture used in or with suture anchors. In exemplary embodiments only, and as detailed above, the suture construct of the present invention may be employed in suture applications that do not involve knot tying, for example, for use with suture anchors (such as PushLock® suture anchor) or for knotless arthroscopic suture repairs (such as knotless single row rotator cuff repair, or SpeedBridge™ repair using no knots and only suture passing steps as described above), among many others.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A method of tissue fixation, comprising:
providing a fixation device having a surgical construct pre-loaded on the fixation device, the surgical construct comprising a flexible loop formed of a flexible strand with two tail regions joined together such that the construct terminates in a same single tail, wherein the surgical construct is formed by threading the flexible strand through an eyelet of the fixation device and then splicing the two tail regions together to terminate in a single tail, and wherein the flexible strand is in the form of a flexible loop with a splice leading to the single tail;
securing the fixation device with the pre-loaded surgical construct into a bone socket;
after the step of securing the fixation device into the bone socket, passing the single tail of the surgical construct through tissue to be repaired at a surgical site;

removing the single tail of the surgical construct to open the loop and release two ends of the flexible strand; and employing at least one of the two ends of the flexible strand to fixate tissue.

2. The method of claim 1, further comprising the step of threading each of the two ends of the flexible strand through an eyelet of another fixation device.

3. The method of claim 1, wherein the fixation device further comprises an anchor body and the eyelet.

4. The method of claim 1, wherein the surgical site is part of a shoulder, a knee, a hip, or an elbow.

* * * * *